United States Patent [19]
Kreindel et al.

[11] Patent Number: 6,162,212
[45] Date of Patent: Dec. 19, 2000

[54] OPTIMAL PROCEDURE FOR PERFORMING A HAIR REMOVAL

[75] Inventors: Michael Kreindel; Shimon Eckhouse, both of Haifa, Israel

[73] Assignee: ESC Medical Systems, Ltd., Yokneam, Israel

[21] Appl. No.: 09/294,753

[22] Filed: Apr. 19, 1999

[51] Int. Cl.⁷ .................................................. A61B 18/18
[52] U.S. Cl. ............................................... 606/9; 606/131
[58] Field of Search .................................... 606/131–133, 606/9, 13

[56] References Cited

U.S. PATENT DOCUMENTS

| | | | |
|---|---|---|---|
| 5,766,214 | 6/1998 | Mehl, Sr. et al. | 606/9 |
| 6,045,548 | 4/2000 | Furumoto et al. | 606/9 |
| 6,050,990 | 4/2000 | Tankovish et al. | 606/9 |
| 6,059,777 | 5/2000 | Acquaire | 606/13 |

*Primary Examiner*—Linda C. M. Dvorak
*Assistant Examiner*—Roy Gibson
*Attorney, Agent, or Firm*—Eitan, Pearl, Latzer & Cohen-Zedek

[57] ABSTRACT

A method for determining an optimal plan of sessions for hair removal treatment. The method includes the steps of receiving information about a hair growth cycle duration of a person to be treated, a duration of the Anagen stage of the person and at least one parameter of a device to be used for performing the treatment, and processing the received information thereby determining at least one of the group including the optimal number of hair removal tretament sessions and the optimal delay between sessions of the treatment.

31 Claims, 3 Drawing Sheets

OPTIMAL PROCEDURE FOR PERFORMING A HAIR REMOVAL

FIELD OF THE INVENTION

The present invention relates generally to hair removal, and more particularly to a method for planning an efficient hair removal treatment.

BACKGROUND OF THE INVENTION

Hair can be removed for cosmetic reasons by various methods. One possible method is heating the hair and the hair follicles to a temperature high enough to result in their coagulation.

Light can be used effectively to remove hair. Light energy is absorbed by the pigment of the hair shaft and then transported as heat to the surrounding tissue. The resulting thermal coagulation of proteins in the hair follicle and other hair supporting structures (i.e., buldge, matrix, blood vessels) prevent subsequent hair growth. It is known that blood is coagulated when heated to the temperature of 70° C. Similarly, heating of the epidermis, the hair and the hair follicle to temperatures of the same order of magnitude will also cause their coagulation and will result in permanent removal of the hair.

The hair growth cycle consists of three stages:

(1) Anagen—the growing stage;
(2) Catagen—transverse stage; and
(3) Telogen—the resting stage.

The Catagen stage lasts only for a relatively short period, therefore it will not be taken into account hereinbelow.

Hair can be efficiently removed only during the Anagen stage. During the Telogen stage, the connection of the hair to its follicles is not strong enough to enable performance of the above described hair removal mechanism.

As shown in FIG. 1, to which reference is now made, the Anagen stage can be devided into three periods, according to the characteristics of the hair growth and the efficiency of the hair removal treatment during each period. In the Initial Period (IP) of the Anagen stage, referenced 1, the hair shaft is too fine and small, so that the energy absorbed by the shaft is not high enough to heat and damage the hair supporting structure, such as the follicle, buldge, etc., and the hair removal treatment cannot be performed efficiently.

In the Final Period (FP) of the Anagen stage, referenced 3, the hair follicle can reach the depth of 4 to 7 mm. Large depth of hair follicle complicates the hair removal treatment, due to limitation of light penetration into the tissue.

The Middle Period (MP) of the Anagen stage, referenced 2, is the optimal time for performing an efficient hair removal treatment.

The efficiency of a hair removal treatment during the different periods of the Anagen stage is schematically shown in FIG. 2.

The efficiency of the treatment is not only a function of the hair growth stage, but depends also on other parameters, such as the characteristics of the device used for hair removal. Possible light sources for performing such a treatment can be any kind of non-coherent light, or coherent light such as: Ruby laser, Alexandrite laser or Diode laser.

FIG. 3 is a schematic illustration of the efficiency of a hair removal treatment performed by a light source with penetration depth smaller than the one of the device used in FIG. 2. As can be seen from comparing FIG. 3 to FIG. 2, the period of time when hair is accessible for a successful hair removal treatment is shorter when the light penetration depth is smaller.

Accordingly, higher light energy, combined with deep light penetration, increases the period of time when hair can be successfully removed. As a result of this, a device including a light source with small energy and small penetration depth requires a larger number of sessions in order to complete an efficient hair removal treatment as opposed to a device including a light source with higher energy. The reason of this is that the period of time such a device can be successfully used is shorter, therefore a smaller quantity of hair can be removed during a single session.

As mentioned above, the efficiency of the hair removal treatment is affected by various parameters, such as the device used for performing the treatment, the location of the treatment and the patient's gender.

Therefore, it is desired to be able to plan the hair removal treatment and to predict the results of each session of the treatment, by taking into account the relevant parameters and their influence on the treatment, for the purpose of performing a more efficient hair removal treatment.

SUMMARY OF THE INVENTION

It is an object of the present invention to provide a method for planning an efficient hair removal treatment.

The present invention provides a method and system for determining the number of sessions of a hair removal treatment and to determine the optimal delay between sessions.

In one embodiment of the present invention, information about the optimal number of sessions and the delay between sessions is provided once parameters of a hair growth cycle duration of a person to be treated, a duration of the Anagen stage of the person and at least one parameter of a device to be used for the treatment are provided.

In another embodiment of the present invention, at least one of the hair growth cycles of a person to be treated and a duration of the Anagen stage are identified based on received information about the gender of the person to be treated and an area on said person's skin to be treated.

Furthermore, in another embodiment of the present invention, the hair removal treatment is simulated by showing the hair growth cycle and the effect of a light pulse on the hair, according to the corresponding parameters. Displaying of the simulation may be performed by using graphic illustration or data presentation.

In yet another embodiment of the present invention, there is provided a system for performing an optimal hair removal treatment, including a hair removal device and a system for determining the optimal number of sessions of a hair removal treatment and the optimal delay between sessions.

The hair removal device may include any non-coherent or coherent light source, such as a ruby laser, an alexandrite laser or a diode laser.

Other objects and advantages of the invention will become apparent upon reading the following detailed description and appended claims, and upon reference to the accompanying drawings.

BRIEF DESCRIPTION OF THE DRAWINGS

The present invention is described with reference to the accompanying drawings, wherein like reference numerals or characters indicate corresponding or like components. In the drawings.

DETAILED DESCRIPTION OF THE PREFERRED EMBODIMENT

Figure 1:
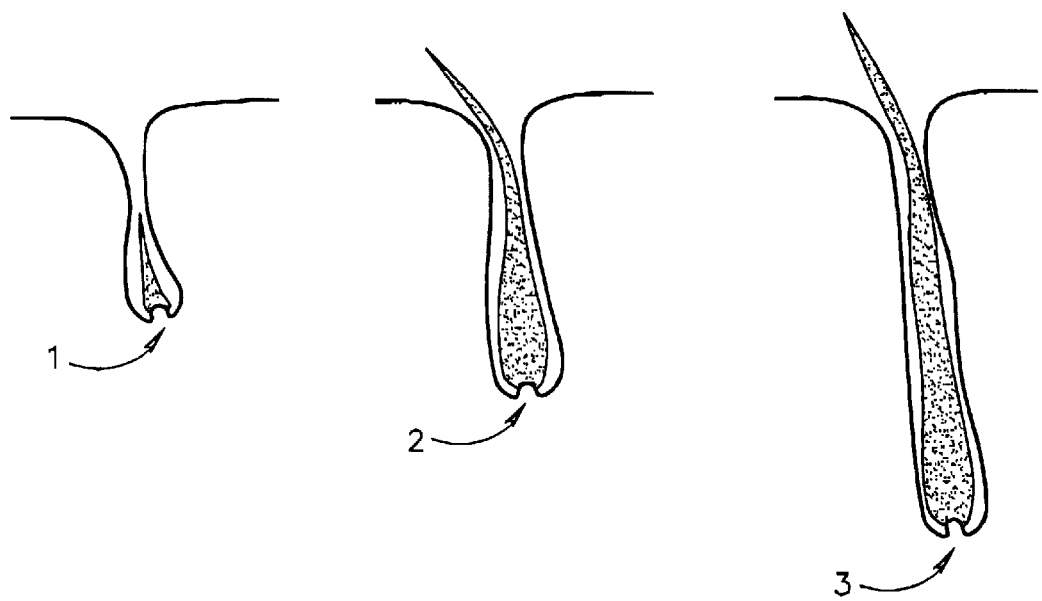
FIG. 1 is a schematic illustration of the hair growth during the Anagen stage.
Figure 2:
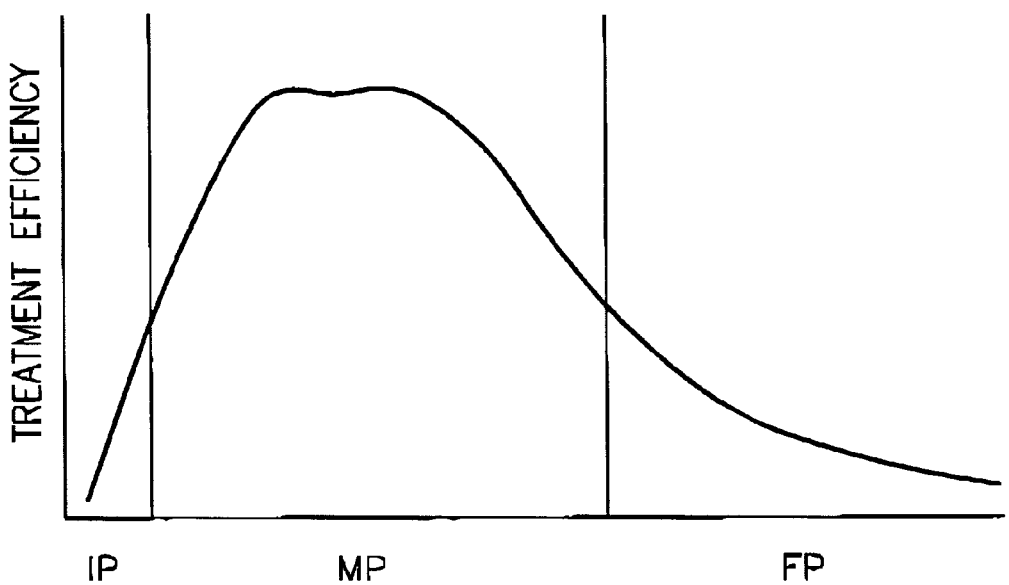
FIG. 2 is a schematic illustration of the treatment efficiency as a function of time during the Anagen stage.
Figure 3:
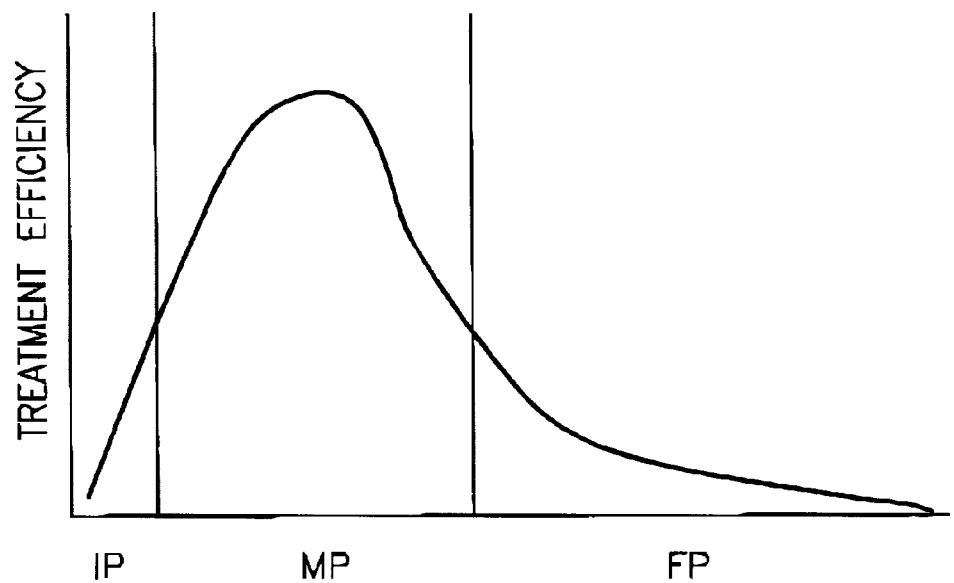
FIG. 3 is a schematic illustration of the treatment efficiency as a function of time during the Anagen stage, when a light source with penetration depth smaller then in FIG. 2 is used.

The present invention provides a method, system and apparatus for determining an optimal session arrangement for performing an efficient hair removal treatment. The method includes the steps of receiving information about a hair growth cycle duration of a person to be treated, a duration of the Anagen stage of the person and at least one parameter of a device to be used for performing the treatment; and processing the received information thereby determining at least one of the group including the optimal number of sessions and the optimal delay between the sessions of the treatment.

The method of the present invention is typically carried out by software or software means (data), executable on computing means, such as a computer (PC) or other similar data processors, microprocessors, embedded processors, microcomputers, microcontrollers, etc. The computing means processes the inputted data, to provide a desired result. Processing includes performing operations, preferably in the form of algorithms, for performing the method of the present invention. One exemplary algorithm for performing the method of the present invention is detailed immediately below. In one non-limiting exemplary embodiment, the method of the present invention can be executed in conjunction with a hair removal system, such as the EpiLight™ hair removal system, manufactured and sold by ESC Medical Systems LTD. of Yokneam, Israel.

Process 1—

The purpose of this process is to provide information about the hair growth cycle and the duration of the Anagen stage. This process is not functional if information about the duration of the hair growth cycle and the Anagen stage of the treated person is provided.

The data available from previous published studies about growth cycle duration as function of the hair location is not uniform, and therefore not reliable. On the other hand, data available from previous published studies about the relative number of hair in the Anagen stage for different gender and different areas of the body is considered reliable, since there are not significant differences between data from different sources. This data can be determined from histology analysis of hair follicles.

The hair growth cycle is calculated based on information about hair regrowth rate. The following parameters are used in the calculation of the hair growth cycle:

N—number of follicles
$n_a$—relative number of hair in the Anagen stage
$t_c$—growth cycle duration
P—percentage of clearance after a single session of the treatment
$N_a$—number of follicles in the Anagen stage
$N_t$—number of follicles in the Telogen stage
$t_t$—Telogen stage duration
$t_a$—Anagen stage duration The dynamic of hair regrowth after a session of the treatment can be described by the following equation:

$$\frac{dN_a}{dt} = \frac{N_t}{t_t} - \frac{N_a}{t_a}(1-P)$$

The above equation shows that in each given state, the number of hairs in the Anagen stage increases because of hair forwarding from the Telogen stage into the Anagen stage, and decreases due to hair leaving the Anagen stage.

By taking into the account the following:

$N_a = n_a N$
$N_t = (1-n_a)N$
$t_a = n_a t_c$
$t_t = (1-n_a)t_c$

The previous equation can be rewritten as follows:

$$\frac{dN}{dt} = \frac{NP}{t_c n_a}$$

As can be seen, if no hair removal treatment is performed, the hair growth is an equilibrium process and $N_a$=const.

By solving the above equation the following results in:

$$N = n_a(1-P)N \exp\left[\frac{(1-P)}{n_a t_c}t\right]$$

This equation is true for a period that is shorter than the growth cycle, since the hair growth changes towards the end of the hair growth cycle. By using this equation, it is possible to calculate the hair growth cycle if the hair clearance after the first session of the hair removal treatment and the regrowth rate are known.

In order to statistically calculate the hair growth cycle for each area of the body, the regression analysis is used. The regression analysis is performed through the different testing results of clearance after the first session and regrowth rate for different body sites by using the general exponential equation:

$$y = c * e^{bx}$$

where c and b are constants.

By comparing this equation to the previous equation, the hair growth cycle as a function of gender and area of the body can be calculated.

Table 1 below shows growth cycles calculated by the way described above, for different hair locations of a female. The table also shows the duration of the Anagen stage as a percentage of the growth cycle, as known from previous studies. In the table, STD represents the standard deviation of the regression analysis method.

TABLE 1

| Location | Duration of Anagen stage | Calculated average growth cycle (in weeks) | Number of patients participating in the study | STD |
|---|---|---|---|---|
| Chin | 70% | 14 | 239 | |
| Upper lip | 65% | 24 | 135 | 30% |
| Axilla | 30% | 61 | 80 | |
| Bikini | 30% | 50 | 137 | |
| Legs | 20% | 48 | 42 | |
| Arms | 20% | 33 | 12 | |

Process 2—

The purpose of this process is to determine the MP period of the Anagen stage.

The MP period of the Anagen stage can be estimated by checking the hair clearance before the second session of the treatment. The clearance before the second treatment, or the MP, is relative to the efficiency of the device and to the duration of the Anagen stage.

Table 2 below shows the hair clearance two months after the first session of the treatment, using different devices while treating a female. The information in the Table is based on clinical studies conducted in the United States. All the devices mentioned in the Table are manufactured and sold by ESC Medical Systems LTD. of Yokneam, Israel. The Epitouch Ruby™ device manipulates a Ruby laser, having a wavelength of 694 nm. The Epitouch Alex™ device manipulates an Alexandrite laser, having a wavelength of 755 nm. The EpiLight™ device manipulates a non-coherent light source, having a wavelength in the range of 590–1200 nm (depending on the filtration). In brackets is noted the number of patients tested in each study.

TABLE 2

| Device | Face (%) | Body (%) | Average (%) |
|---|---|---|---|
| Epitouch Ruby ™ | 24.5 (305) | 30 (95) | 25 (400) |
| Epitouch Alex ™ | 28 (77) | 36 (49) | 35 (126) |
| EpiLight ™ | 50 (79) | 46 (53) | 48 (132) |

For performing this process, the duration of the Anagen stage can be provided for each person to be treated or alternatively, it can be identified based on previous published studies and according to provided information about the gender of the person to be treated and the area of the body to be treated.

For example, for a female, it is known that the Anagen stage of the face area is 70% of the growth cycle, meaning 70% of the hair growing on the face is always in the Anagen stage. As mentioned above, the MP(%) is different for each device. For example, in the face area, the Epilight™ device removes 50% of the hair in the Anagen stage. Therefore, the MP(%) is 50% of the Anagen stage, or 35% of the growth cycle. The same value for the Epitouch Alex™ device is: MP(%)=28% of Anagen stage ~20% of the growth cycle. The same value for Epitouch Ruby™ device is: MP(%)= 24% of the Anagen stage, which is about 17% of the growth cycle.

Process 3—

The purpose of this process is to calculate the number of sessions needed in order to complete a successful hair removal treatment.

The total number of sessions (NT) can be calculated by the following equation:

$$NT = \frac{1}{n_a MP}$$

As mentioned above, $n_a$ represents the relative quantity of hair in the Anagen stage.

Table 3 below shows the average number of sessions needed to complete a hair removal treatment as a function of the location of the treatment and the device used, for a female.

TABLE 3

| | Average number of sessions | |
|---|---|---|
| Device | Face | Body |
| Epitouch Ruby ™ | 7 | 16 |
| Epitouch Alex ™ | 6 | 14 |
| EpiLight ™ | 4 | 11 |

Process 4—

The purpose of this process is to calculate the delay needed between each of the sessions of the treatment in order to allow hair regrowth.

The MP influences also on the delay needed between sessions. The delay between sessions (D) can be calculated as follows:

$$D = MP n_a t_c$$

Table 4 below shows the average delay in weeks needed between sessions, as a function of the location of the treatment and the device used, for a female.

TABLE 4

| | Average delay between sessions (in weeks) | |
|---|---|---|
| Device | Face | Body |
| Epitouch Ruby ™ | 3 | 3 |
| Epitouch Alex ™ | 4 | 4 |
| EpiLight ™ | 6 | 5 |

Figure 4:
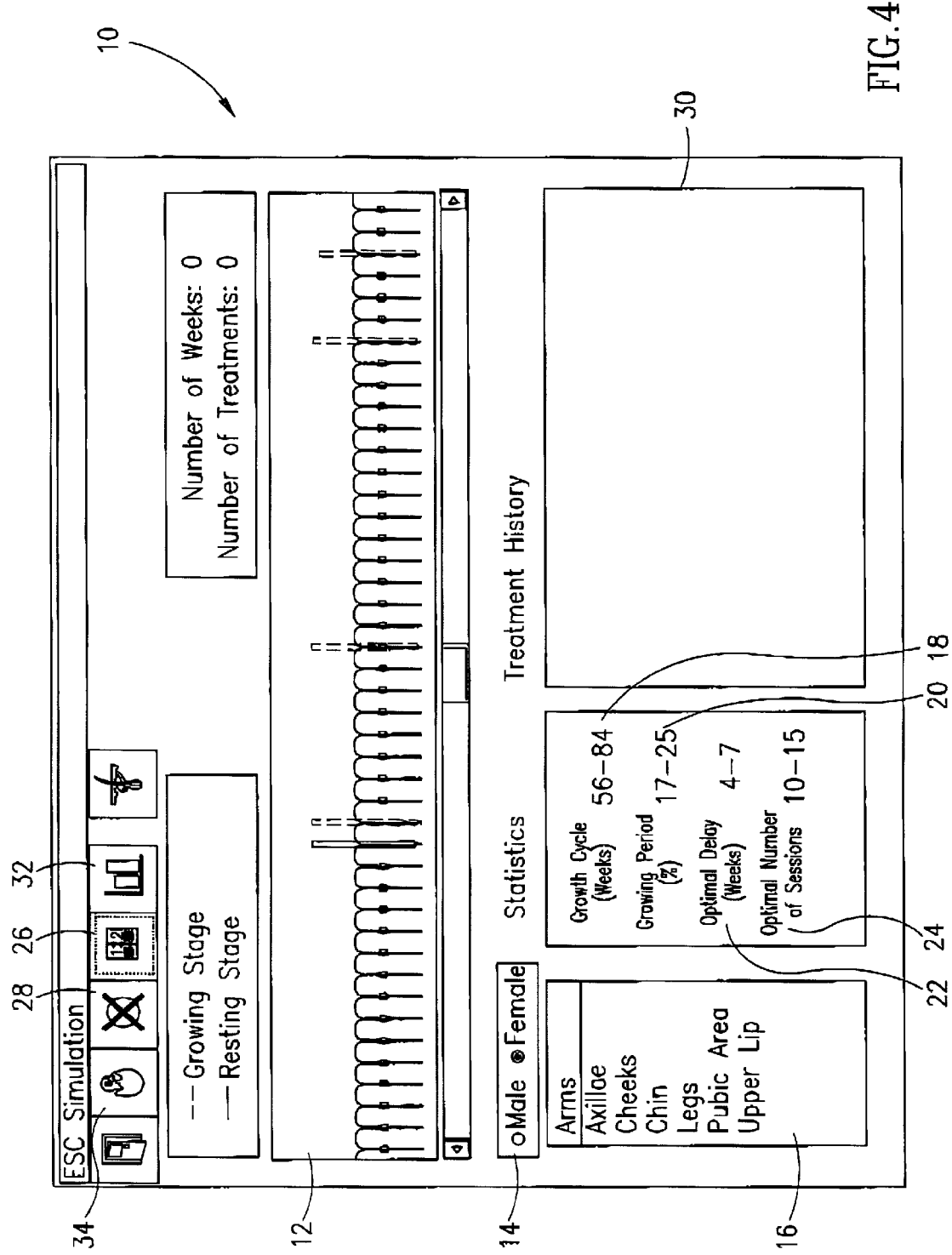
FIG. 4 is a schematic illustration of a display screen of a processor according to a preferred embodiment of the present invention.

FIG. 4 is a schematic illustration of a display screen of a processor where a preferred embodiment of the method of the present invention is executed.

On the main screen 10, a graphic illustration 12 is shown, which describes randomly the approximate ratio between hair in the Anagen stage (dotted lines) and hair in the Telogen stage (lines). After entering parameters concerning the gender of the patient (14), the hair location (16) and the efficiency of the device used for performing the treatment (not shown), information about hair growth cycle (18) and duration of each growth stage (20) is provided, and the graphic illustration changes accordingly. Further, optimal delays between sessions and number of sessions, 22 and 24 accordingly, are suggested. By clicking the button referenced 26, the dynamic of hair growth can be observed. Each pressing on this button simulates by using the graphic illustration 12 hair regrowth one week ahead. A session of the treatment, meaning applying a pulse of light, is simulated on the graphic illustration 12 by pressing the "Pulse" button 28. After clicking on the button 28, each hair that is in the MP period of the Anagen stage disappears, and the information about the follicles clearance and visible hair clearance appears in the "History Treatment" field 30. The dynamic of the visible hair and follicles can be seen also on a chart by clicking the "Graph" button 32. By clicking the "New Patient" button 34 the data is refreshed, a new graphic illustration appears, and new parameters can be inserted, resulting in new data.

Although the invention has been described in conjunction with a specific embodiment thereof, it is evident that many alternatives, modifications and variations will be apparent to those skilled in the art thereof without departing from the spirit or scope thereof. Accordingly, it is intended to embrace all such alternatives, modifications and variations that fall within the spirit and broad scope of the appended claims.

What is claimed is:

1. A method for determining the optimal plan of sessions for a hair removal treatment, comprising the steps of:
   receiving information about a hair growth cycle duration of a person to be treated, duration of an Anagen stage of said person and at least one parameter of a device to be used for performing said treatment; and
   processing said received information thereby determining at least one of the group comprising an optimal number of sessions and an optimal delay between sessions of said hair removal treatment.

2. The method according to claim 1 further comprising the step of providing a database identifying hair growth cycle duration and duration of the Anagen stage according to gender and area of the body.

3. The method according to claim 2 wherein at least one hair growth cycle of a person to be treated and said duration of the Anagen stage of said person is identified based on received information about a gender of a person to be treated and an area on said person's skin to be treated.

4. The method according to claim 1 wherein said at least one parameter of a device to be used for performing said treatment is efficiency of the device.

5. The method according to claim 1 further comprising the step of controlling a display device to display said optimal plan of sessions of hair removal treatment.

6. A method for simulating sessions of a hair removal treatment, comprising the steps of:
   receiving information about a hair growth cycle of a person to be treated, a duration of an Anagen stage of said person and at least one parameter of a device to be used for performing said treatment; and
   processing said received information thereby simulating at least one of the group comprising hair growth and results of a session of the hair removal reatment.

7. The method according to claim 6 further comprising the step of providing a database identifying hair growth cycle duration and duration of the Anagen stage according to gender and area of the body.

8. The method according to claim 7 wherein at least one of said hair growth cycle of a person to be treated and said duration of the Anagen stage of said person is identified based on received information about a gender of a person to be treated and an area on said person's skin to be treated.

9. The method according to claim 6 wherein said at least one parameter of a device to be used for performing said treatment is efficiency of the device.

10. The method according to claim 6 further comprising the step of controlling a display device to display at least one of said simulations.

11. The method according to claim 10 wherein the step of controlling a display device comprises the step of displaying by using graphic illustrations.

12. The method according to claim 10 wherein the step of controlling a display device comprises the step of displaying by using data presentation.

13. A system for determining the optimal plan of sessions for a hair removal treatment, comprising:
   a storage device; and
   a processor programmed to:
      (a) receive information about a hair growth cycle duration of a person to be treated, a duration of an Anagen stage of said person and at least one parameter of a device to be used for performing said treatment; and
      (b) process said received information to determine at least one of the group comprising an optimal number of sessions and an optimal delay between sessions.

14. The system according to claim 13 wherein said processor is further programmed to maintain in the storage device a database identifying hair growth cycle duration and duration of the Anagen stage according to gender and area of the body.

15. The system according to claim 14 wherein said processor is further programmed to receive information about a gender of a person to be treated and an area on said person's skin to be treated; and
   identify at least one of said hair growth cycle of a person to be treated and said duration of the Anagen stage of said person based on said received information about a gender of a person to be treated and an area on said person's skin to be treated.

16. The system according to claim 13 wherein said at least one parameter of a device to be used for performing said treatment is efficiency of the device.

17. The system according to claim 13 further comprising display means and wherein the processor is further programmed to control said display means to display said optimal plan of sessions for hair removal treatment.

18. A system for simulating sessions of a hair removal treatment, comprising:
   a storage device;
   a processor programmed to:
      (a) receive information about a hair growth cycle duration of a person to be treated, a duration of an Anagen stage of said person and at least one parameter of a device to be used for performing said treatment; and
      (b) process said received information to simulate at least one of the group comprising the hair growth cycle and results of a session of the hair removal treatment.

19. The system according to claim 18 wherein said processor is further programmed to maintain in the storage device a database identifying hair growth cycle duration and duration of the Anagen stage according to gender and area of the body.

20. The system according to claim 19 wherein said processor is further programmed to receive information about a gender of a person to be treated and an area on said person's skin to be treated; and
   identify at least one of said hair growth cycle of a person to be treated and said duration of the Anagen stage of said person based on said received information about a gender of a person to be treated and an area on said person's skin to be treated.

21. The system according to claim 18 wherein said at least one parameter of a device to be used for performing said treatment is efficiency of the device.

22. The system according to claim 18 further comprising display means and wherein the processor is further programmed to control said display means to display at least one of said simulations.

23. The system according to claim 22 wherein the processor is further programmed to control said display means to display at least one of said simulations by using graphic illustrations.

24. The system according to claim 22 wherein the processor is further programmed to control said display means to display at least one of said simulations by using data presentation.

25. A system for performing an optimal hair removal treatment, comprising:
   a hair removal device;

a storage device; and a processor programmed to:
- (a) receive information about a hair growth cycle duration of a person to be treated, a duration of an Anagen stage of said person and least one parameter of a device to be used for performing said treatment; and
- (b) process said received information to determine at least one of the group comprising an optimal number of sessions and an optimal delay between sessions.

26. The system according to claim 25 wherein said processor is further programmed to maintain in the storage device a database identifying hair growth cycle duration and duration of the Anagen stage according to gender and the area of the body.

27. The system according to claim 26 wherein said processor is further programmed to receive information about a gender of a person to be treated and an area on said person's skin to be treated; and identify at least one of said hair growth cycle of a person to be treated and said duration of the Anagen stage of said person based on said received information about a gender of a person to be treated and an area on said person's skin to be treated.

28. The system according to claim 25 wherein said at least one parameter of a device to be used for performing said treatment is efficiency of the device.

29. The system according to claim 25 further including display means and wherein the processor is further programmed to control said display means to display said optimal plan of sessions of hair removal treatment.

30. The system according to claim 25 wherein the hair removal device is a device comprising a non-coherent light source.

31. The system according to claim 25 wherein the hair removal device is a device comprising a coherent light source, such as any of the group consisting of a ruby laser, an alexandrite laser and a diode laser.

* * * * *